(12) United States Patent  
Sacca

(10) Patent No.: US 6,969,497 B2  
(45) Date of Patent: Nov. 29, 2005

(54) DECONTAMINATION SYSTEM FOR USE WITH A RAPID TRANSFER PORT

(76) Inventor: Giuseppe Sacca, 24241 Tama La., Laguna Niguel, CA (US) 92677

( * ) Notice: Subject to any disclaimer, the term of this patent is extended or adjusted under 35 U.S.C. 154(b) by 630 days.

(21) Appl. No.: 10/190,860

(22) Filed: Jul. 8, 2002

(65) Prior Publication Data

US 2004/0005259 A1 Jan. 8, 2004

(51) Int. Cl.[7] ................................................ A61L 2/00
(52) U.S. Cl. ...................... 422/300; 422/292; 422/295; 422/298; 422/305; 422/307; 312/1
(58) Field of Search ................................ 422/292, 295, 422/298, 300, 305, 307; 312/1

(56) References Cited

U.S. PATENT DOCUMENTS

| | | | |
|---|---|---|---|
| 4,169,123 A | | 9/1979 | Moore et al. |
| 5,139,318 A | * | 8/1992 | Broxup ........................... 312/1 |
| 5,441,708 A | * | 8/1995 | Diccianni et al. ........... 422/292 |
| 5,460,439 A | | 10/1995 | Jennrich et al. |
| 5,732,843 A | | 3/1998 | Glachet et al. |
| 5,783,156 A | | 7/1998 | Renzi et al. |
| 5,906,801 A | | 5/1999 | Goughnour |

* cited by examiner

Primary Examiner—John Kim  
Assistant Examiner—Brad Y. Chin

(57) ABSTRACT

The system includes an enclosure for providing a closed volume for bactericide vapor. The enclosure has a container access opening formed therein for providing vapor communication between a container and the closed volume. A container interface assembly at the container access opening positions, locks and seals the container to the enclosure. A container door removal system is partially contained within the enclosure and is operably engaged with the enclosure and attachable to a container door of the container for separating the container door from the container. The container door removal system includes an actuator element located external to the enclosure. A vapor injection system is included having an inlet and an outlet for the bactericide vapor. During operation, a container is attached to the container interface assembly and the container door is separated from the container by operating the actuator element of the container door removal system providing vapor communication between the closed volume and the volume within the container. The bactericide vapor may be introduced into the enclosure and the container via the vapor injection system.

21 Claims, 17 Drawing Sheets

DECONTAMINATION SYSTEM FOR USE WITH A RAPID TRANSFER PORT

BACKGROUND OF THE INVENTION

1. Field of the Invention

This invention relates to rapid transfer port (RTP) systems and more particularly to the decontamination of transfer containers for use with such rapid transfer port (RTP) systems. The RTP systems are of a type for transferring articles between two environments (such as an isolator barrier system and a transfer container) that are adapted to be brought into close proximity to one another by a docking operation.

2. Description of the Related Art

Certain manufacturing processes require the maintenance of separation between two environments to avoid contamination of the cleaner of the two environments by the dirtier of the two. This is accomplished with the use of environments such as isolation barriers. For example, in the case of certain pharmaceutical products, the manufacturing process is performed within these isolation barriers to prevent contamination of the product being produced by dust particles, bacteria and viruses which are found in the outside ambient air. The same holds true for the assembly of certain medical devices. In the case of radioactive operations or bacteriological procedures, the environment within the isolation barrier is dirty as compared to the outside ambient air. In these cases, the isolation barrier serves the function of keeping the product being handled from escaping into the external environment.

In recent years, in the pharmaceutical industry, because of the expense and operational difficulties of maintaining so-called "clean rooms" into which operators enter to carry out procedures, the use of isolation barriers has become common practice. The isolation barriers, in concept large glove boxes, are integrated onto the machinery used to carry out the necessary manufacturing operations. A variation of these isolation barriers is what is commonly known as a RABS, Restricted Access Barrier System.

Means for transferring components, product, supplies, etc. into and out of these isolation barriers without risk of contamination of the components being transferred by the "dirty" external environment during the docking and components transfer process must be provided. To accomplish this, isolator barrier systems and RABS feature devices generally called Rapid Transfer Ports (RTP). These RTP devices may be of various type, size and configuration. A common type of RTP device is one that is offered by the French company La Calhene, referred to as the DPTE. This device requires rotation of the transfer container during the docking process. This type of RTP device is generally mounted on an outer surface of the isolation barrier and features docking attachments for a pre-sterilized transfer container housing the components to be transferred. Upon the docking process, the operator places the transfer container into alignment with the RTP and rotates the container approximately 60 degrees to complete the docking operation. The docking process firmly attaches the transfer container to the RTP and, simultaneously, the transfer container door to the RTP door. Once docked, the operator reaches inside the isolation barrier via gloves located on the isolation barrier wall and opens the RTP door, with it attached the transfer container door, and gains access to the components located within the transfer container. To prevent contamination of the "clean" environment, the docking process places the "dirty" surfaces of the RTP and of the transfer container in sealed contact with each thus not permitting "dirty" particles to escape into the "clean" environment.

The container must be sterilized prior to docking to a sterile isolator barrier. The sterilization process can be a lengthy operation and can therefore be considered a obstacle in meeting the manufacturing flow requirements of the operation. Presently, the sterilization process of the container is accomplished by following one of two basic methods: sterilization using steam or vapor hydrogen peroxide (VHP) bactericide vapor.

VHP gas is produced by an appropriate VHP generator which transform the hydrogen peroxide from its fluid form to the vapor form necessary to cover all surfaces to be sterilized and creates a continuous flow of the gas though the device to be sterilized by means of flow components and proper injection connections.

With either one of the methods of container sterilization, the access door of the RTP container is removed from its receptacle in the container's forward flange to make sure of total coverage by the sterilant (either the steam or the bactericide vapor) of the critical surfaces between the door and the container flange.

Sterilization using steam is normally done inside a steam autoclave. The container is placed on a cart inside an autoclave, the door is removed from the container and a steam sterilization cycle is conducted. At the conclusion of the sterilization cycle, the container is transferred to an isolator which is connected to the exit door of the steam autoclave. An operator, through gloves, can then install the door onto the container thus creating a sterile closed volume within the container. From this point on the canister is ready for use. This sequence requires quite a number of time consuming process steps and it must take place in an autoclave which is normally used to sterilize all parts, availability of this critical piece of equipment is an operational issue in particular for those operations which require continuous flow of sterile canisters.

An alternate method of sterilizing a container using steam is that disclosed in Glachet et al U.S. Pat. No. 5,732,843. The device clamps onto the access door end of the canister to be sterilized and permits removal of the access door to allow coverage of all surfaces by the steam. The steam is introduced into the container by ports located in the container itself. Although capable of steam sterilizing the container, the device requires the container to feature steam injection ports, it is limited in use to a specific type of containers and requires the relative lengthy steam sterilization process to take place. It is seen that, for those applications where quick turn around of the container sterilization cycle is critical to the operation, the system has limitations.

The second method of sterilizing the container prior to use is to expose the surfaces to be sterilized to a bactericide vapor, normally vapor hydrogen peroxide (VHP). This process is normally referred to as a process of decontamination. VHP decontamination of containers is normally done by connecting the container to an RTP port of the isolator barrier where the sterile work takes place, by opening the door of the container while its is attached to the door of the RTP port to which the container is docked and by injecting the whole chamber (isolator barrier and container) with the bactericide vapor. This process of decontamination is quite lengthy and is limited to the one container that is docked to the isolator barrier during the decontamination process. This approach does not work well for those applications which require continuous flow of containers to support the manufacturing process.

A second method of decontaminating the container with vapor hydrogen peroxide is to make use of the same device previously discussed that is disclosed in Glachet et al U.S. Pat. No. 5,732,843. The device and its use have some restrictions which one might consider to be operationally undesirable; specifically, the device requires the presence of inlet and outlet openings in the container itself, thus placing limitations on the configuration of the container itself. In addition, the device does not include means for proper distribution of the bactericide vapor over all surfaces of the door end of the container and the system creates a volume that is of such small magnitude that existing VHP generator technology could experience difficulties in maintaining proper positive pressure during the decontamination cycle.

SUMMARY

The present invention is a system for decontaminating a container of a type that interfaces with a rapid transfer port (RTP). In a broad aspect, the present invention includes an enclosure for providing a closed volume for bactericide vapor. The enclosure has a container access opening formed therein for providing vapor communication between a container and the closed volume. A container interface assembly at the container access opening positions, locks and seals the container to the enclosure. A container door removal system is partially contained within the enclosure. It is operably engaged with the enclosure and attachable to a container door of the container for separating the container door from the container. The container door removal system includes an actuator element located external to the enclosure. A vapor injection system is secured to the enclosure. It comprises an inlet and an outlet for the bactericide vapor. During operation, a container is attached to the container interface assembly and the container door is separated from the container by operating the actuator element of the container door removal system providing vapor communication between the closed volume and the volume within the container. The bactericide vapor may be introduced into the enclosure and the container via the vapor injection system.

There are manufacturing operations that require a continuous flow of decontaminated RTP canisters. Operations such as rejects removal, production supplies introduction and change out parts introduction consist of docking a decontaminated RTP canister to the isolator system, performing the required operations and undocking it without affecting the integrity of the isolator system itself. As explained above, the prior art requires using either an autoclave or an entire isolator to decontaminate the RTP canister prior to use. Using these pieces of equipment to perform the decontamination process is inefficient from a manufacturing flow standpoint.

The present invention allows the user to decontaminate the RTP canister without impacting the usage requirements of either the autoclave or the isolator system. Because the decontamination unit is dedicated to decontaminating a single canister, the time necessary to complete a decontamination cycle is very brief, thus permitting a continuous flow of canisters as required by the manufacturing process.

It is possible that some manufacturing operations have a demand for decontaminated RTP canisters which is in excess of the output of a single decontamination unit. An example of such an operation may be an installation with multiple filling lines operating simultaneously. The modular design of the present invention is such that multiple decontamination units can be connected to a single VHP gas generator, as required by the manufacturing flow.

Other objects, advantages, and novel features will become apparent from the following detailed description of the invention when considered in conjunction with the accompanying drawings.

Other objects, advantages, and novel features will become apparent from the following detailed description of the invention when considered in conjunction with the accompanying drawings.

DETAILED DESCRIPTION OF THE INVENTION

Figure 1:
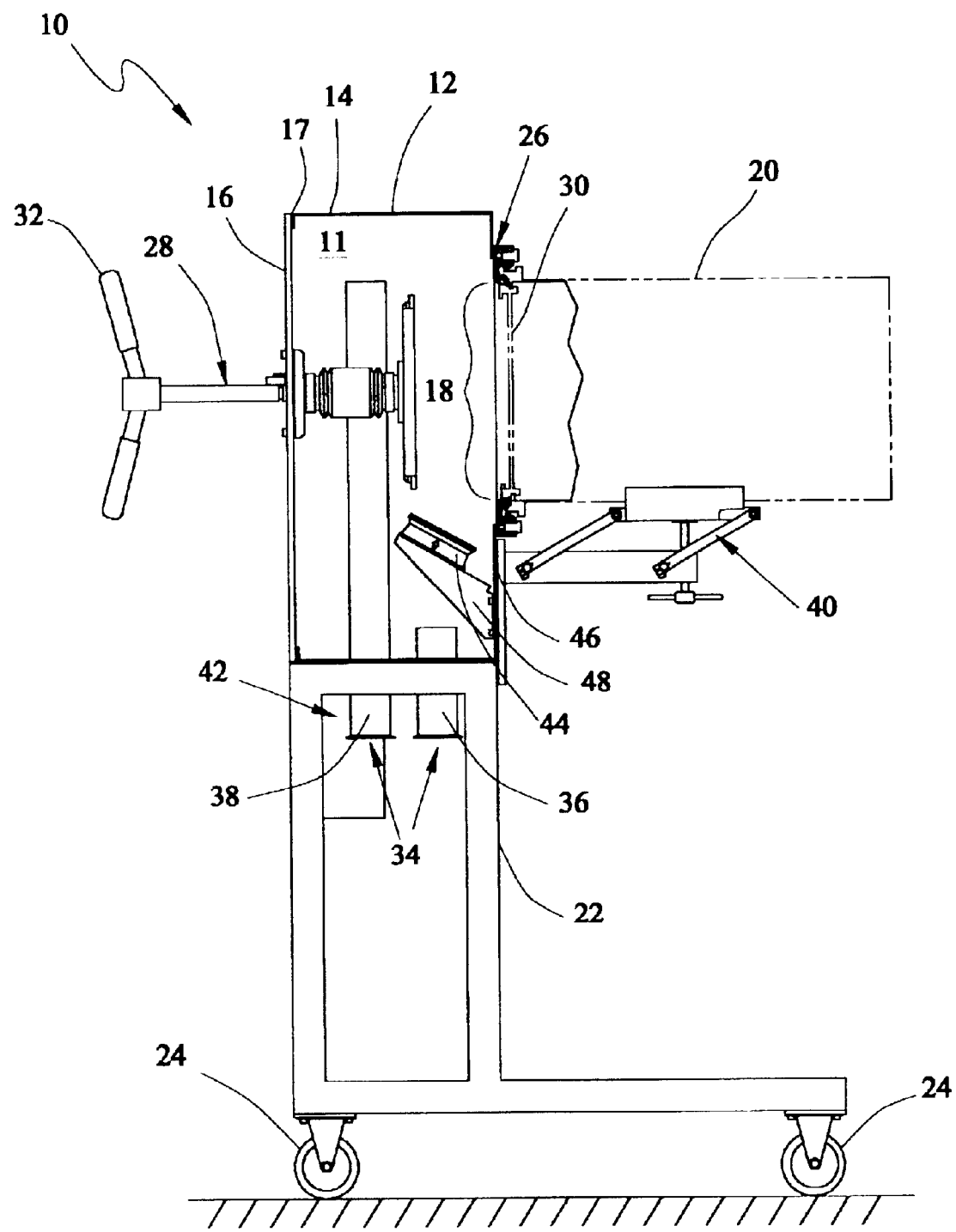
FIG. 1 is a side view of the present invention with the enclosure outer cover removed, the invention being shown in a standby configuration, the container assembly being shown in phantom.
Figure 2:
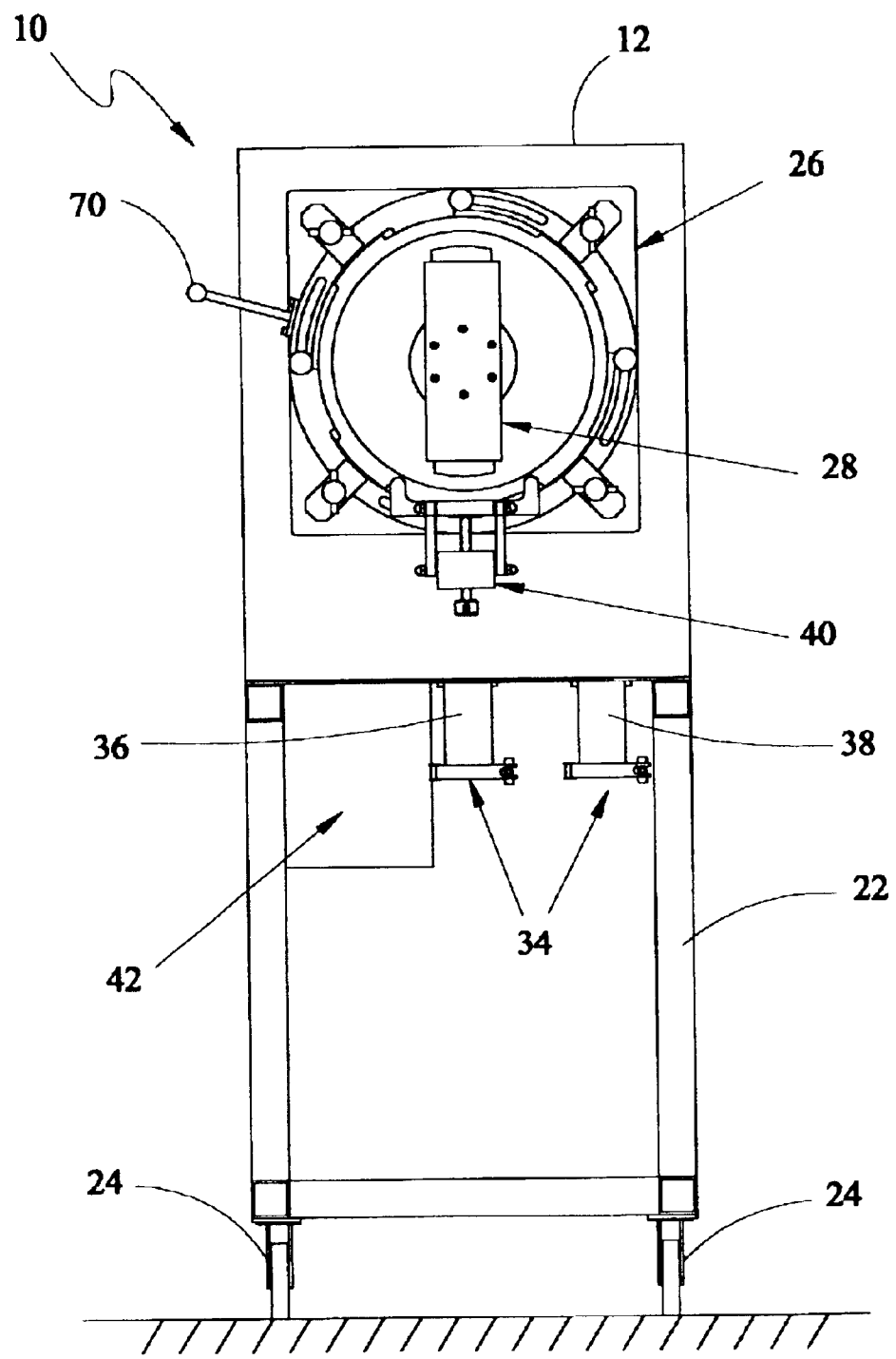
FIG. 2 is the front view of the present invention.

Referring to the drawings and the characters of reference marked thereon, FIGS. 1–2 illustrate a preferred embodiment of the system for decontaminating a container, of the present invention, designated generally as 10. The system 10 includes an enclosure 12 for providing a closed volume 11 for bactericide vapor. The enclosure 12 preferably includes a stainless steel outer skin 14 and a transparent portion 16. The transparent portion 16 provides an internal view of the enclosure 12. The transparent portion 16 is attached by means of a silicone gasket 17. The enclosure 12 has a container access opening 18 formed therein for providing vapor communication between a container 20 and the closed volume 11. The enclosure 12 is supported by a welded tubular frame 22, which preferably has casters 24 for ease of system movement.

A container interface assembly, designated generally as 26, is located at the container access opening 18 for positioning, locking and sealing the container 20 to the enclosure 12. A container door removal system, designated generally as 28, is partially contained within the enclosure 12. It is operably engaged with the enclosure 12 and attachable to a container door 30 of the container 20 for separating the container door 30 from the container 20. The container door removal system 28 includes an actuator element 32 located external to the enclosure 12.

A vapor injection system, designated generally as 34, is secured to the enclosure 12, which includes an inlet 36 and an outlet 38 for the bactericide vapor. A container support device 40 is also attached to the enclosure 12. The container support device 40 is adjustable in a vertical direction for aligning the container 20 to the container interface assembly 26. A control box 42 is preferably attached to the enclosure 12, as will be discussed in detail below. A mixing fan 44 is preferably contained within the enclosure 12. The mixing fan 44 is attached to a front wall 46 of the enclosure 12 by means of an angled mounting bracket 48. It is angled to maximize mixing of bactericide vapor within the enclosure 12.

Figure 3:
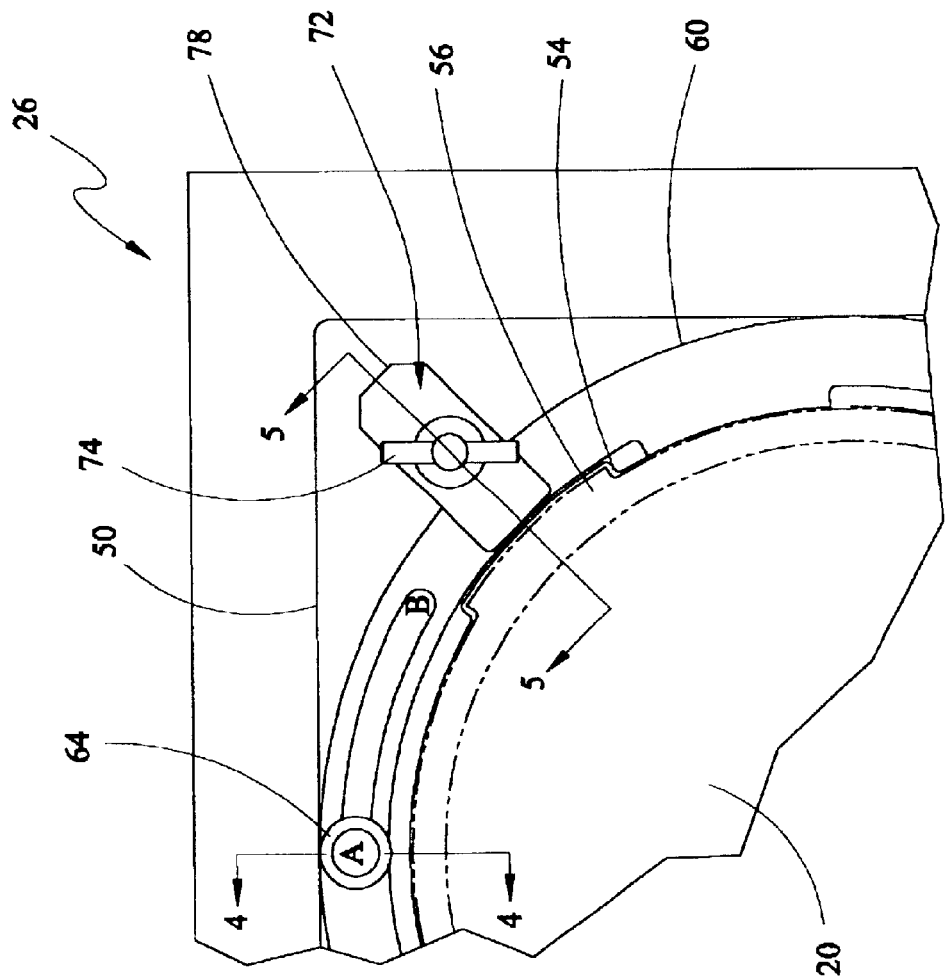
FIG. 3 is a partial view of the container interface assembly showing a close up of its upper right quadrant. The container assembly is shown in phantom.
Figure 4:
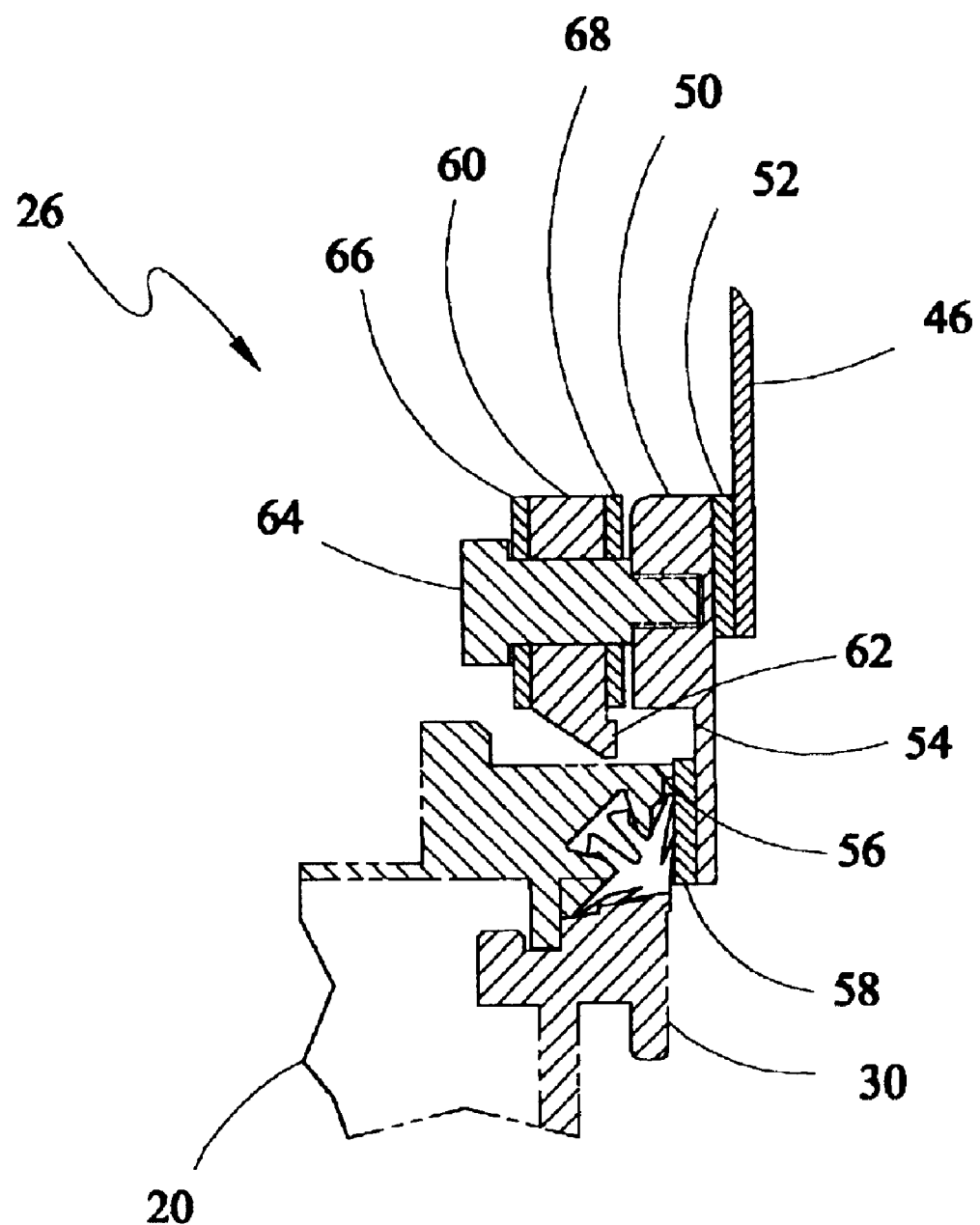
FIG. 4 is a partial cross-sectional view of the container interface assembly, shown along line 4—4 of FIG. 3.
Figure 5:
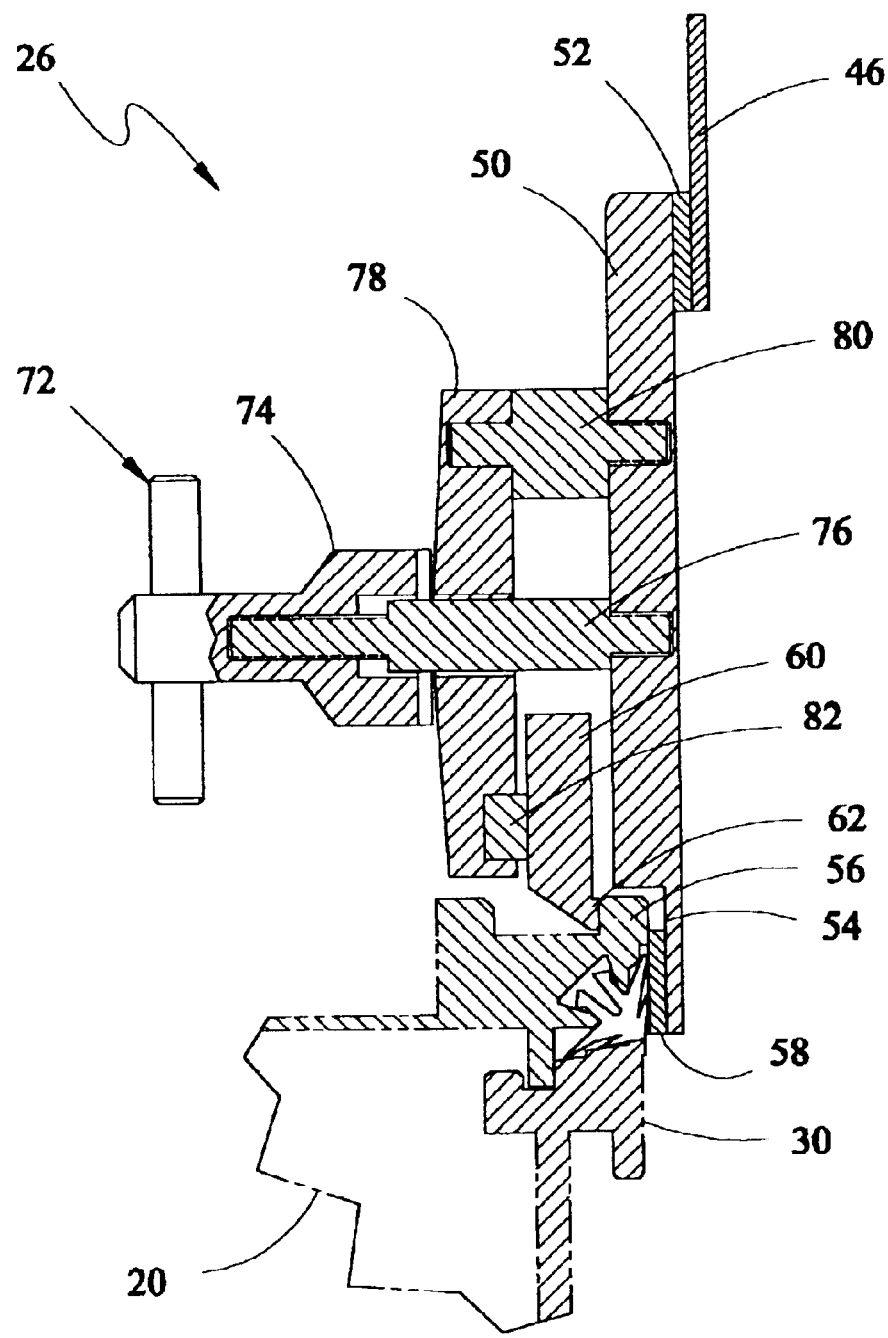
FIG. 5 is a partial cross-sectional view of the container interface assembly, shown along line 5—5 of FIG. 3.

Referring now to FIGS. 3–5 the container interface assembly 26 is shown in more detail. An interface plate 50 is attached to the front wall 46 of the enclosure 12. A gasket 52 is positioned between the interface plate 50 and the front wall 46 of the enclosure 12. The interface plate 50 forms a receptacle 54 for a forward flange 56 of the container 20. A seal 58 creates an airtight connection between the receptacle 54 and the forward flange 56. The seal 58 may be formed of silicone rubber or other conventional sealing material. A rotatable ring 60 engages the forward flange 56. The rotatable ring 60 includes a lug 62 that engages and compresses the forward flange 56. The rotatable ring 60 is free to rotate between positions A and B. At position A, the container 20 forward flange 56 is not engaged by the lug 62 of the rotatable ring 60. At position B, the lug 62 engages the forward flange 56. Rotation of the rotatable ring 60 between position A and position B is set by pin 64. Washers 66, 68, provide protection from wear. Rotation of the rotatable ring 60 is provided by manual handle 70 (see FIG. 2).

A set of lockdown fastener assemblies 72 is connected to the interface plate 50 for compressing the rotatable ring 60 onto the forward flange 56. Each lockdown fastener assembly 72 includes a lockdown nut 74, a threaded stud 76, a clamp bar 78 and a pivot pin 80. Clamp bar 78 includes a Teflon pressure pad 82. Turning locking nut 74 tilts clamp bar 78 about pivot pin 80 creating a clamping force onto rotatable ring 60.

Figure 6:
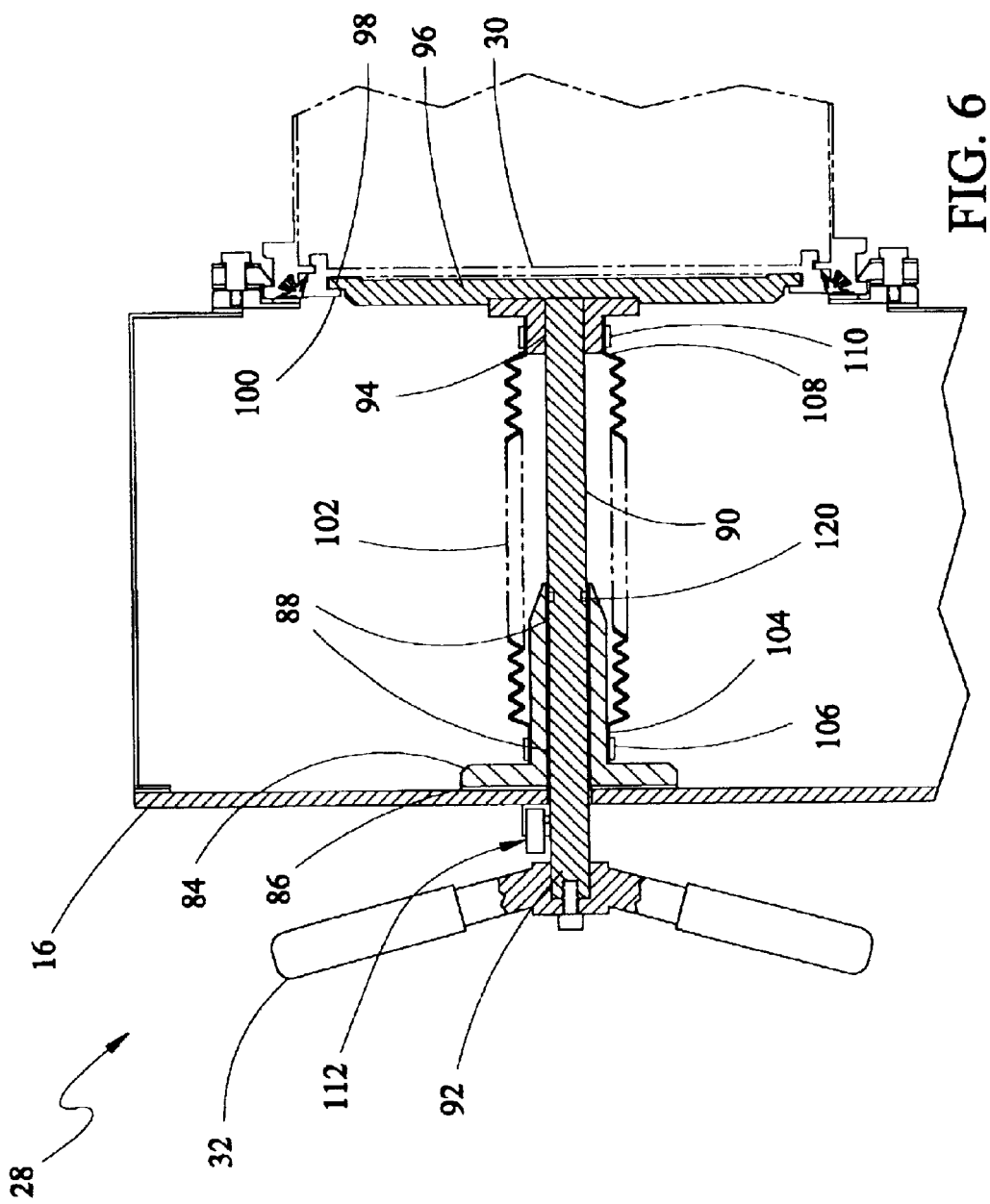
FIG. 6 is a partial cross-sectional view of the present invention showing a close up of the container door removal system. The container assembly is shown in phantom.
Figure 7:
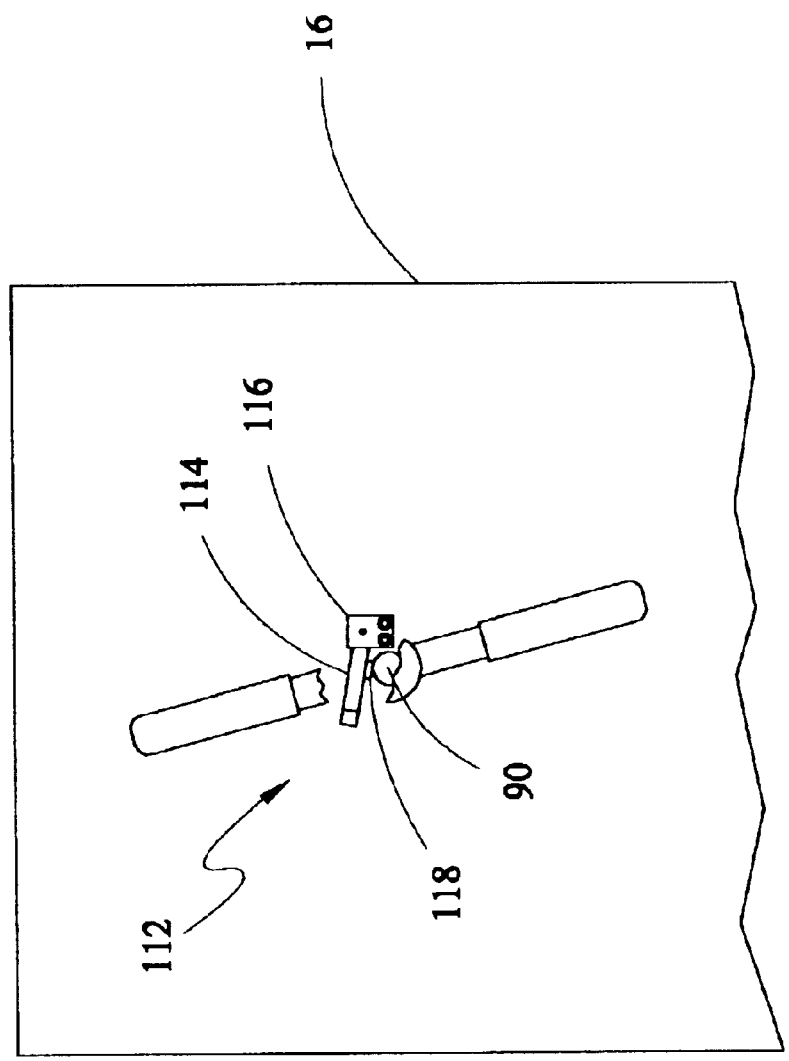
FIG. 7 is a rear view of the container door removal system, with a portion of the actuator element removed to show the shaft positioning system.

Referring now to FIGS. 6 and 7 the container door removal system 28 is shown in more detail. A flanged cylindrical member 84 is in fixed engagement with the transparent portion or rear wall 16 of the enclosure. Although the invention is shown with the transparent portion comprising the entire rear wall it may optionally comprise only a portion of it, as desired for the intended application. A gasket 86 is positioned between the flanged cylindrical member 84 and the transparent portion 16. The flanged cylindrical member 84 has plastic bushings 88.

A shaft 90 is positioned within and in sliding engagement with the flanged cylindrical member 84. The shaft 90 includes a shaft external end 92 and a shaft internal end 94. The actuator element 32 is attached to the shaft external end 92. A container door engagement plate 96 is attached to the shaft internal end 94. Container door engagement plate 96 includes protrusions 98 which engage container door indentations 100.

A bellows 102 is attached at a first end 104 of the flanged cylindrical member 84 by means of a clamp 106. Bellows 102 is attached at a second end 108 to the container door engagement plate 96 by means of a clamp 110.

A shaft positioning system 112 includes a flat bar 114 free to pivot in the vertical direction within attachment block 116. Attachment block 116 is in fixed engagement with the transparent portion or rear wall 16 of the enclosure. The flat bar 114 includes an engagement protrusion 118 which is free to engage the elongated indentation 120 of shaft 90 thus providing desired positioning of shaft 90 within flanged cylindrical member 84.

Figure 8:
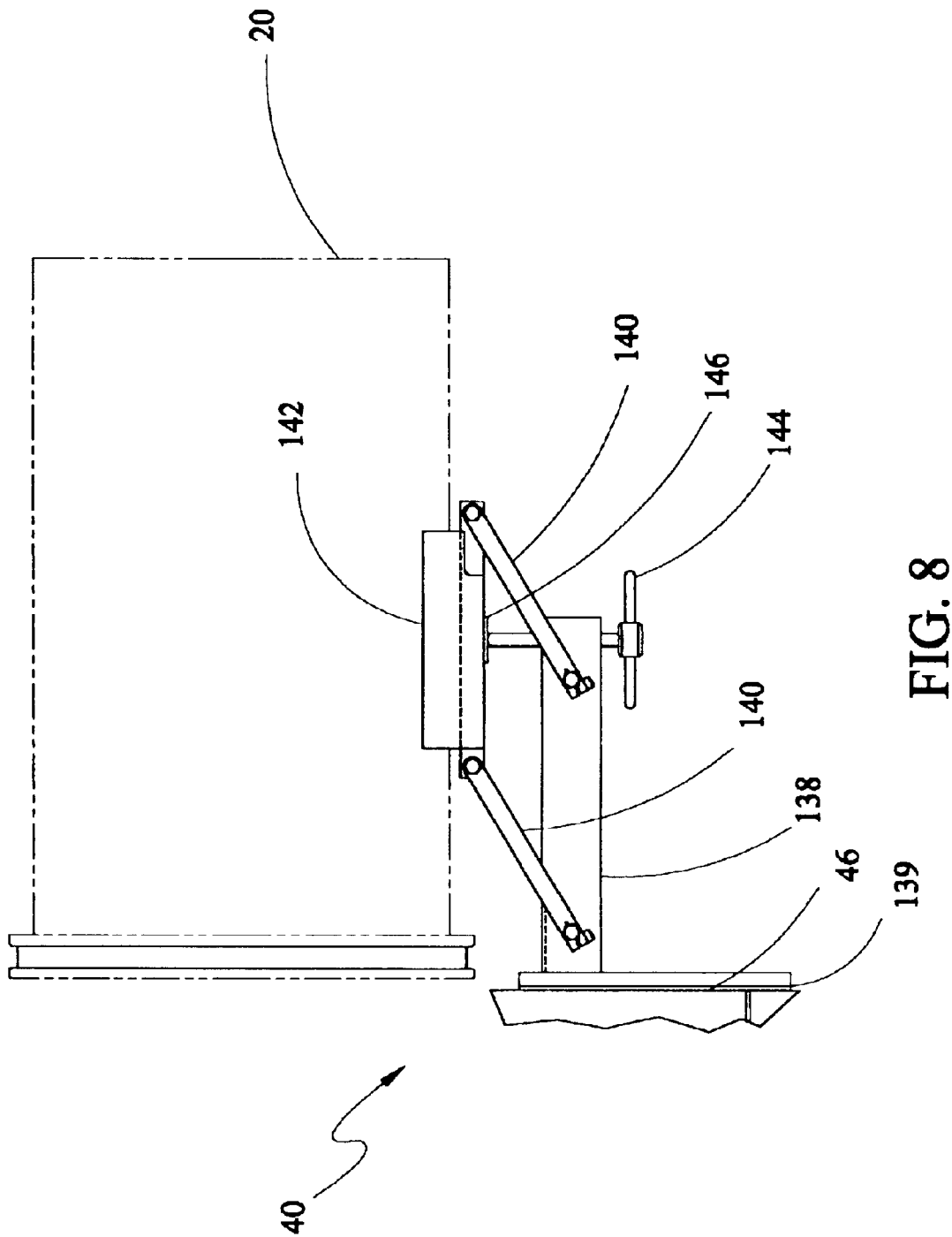
FIG. 8 is a side view of the present invention showing a close up of the container vertical support system. The container assembly is shown in phantom.
Figure 9:
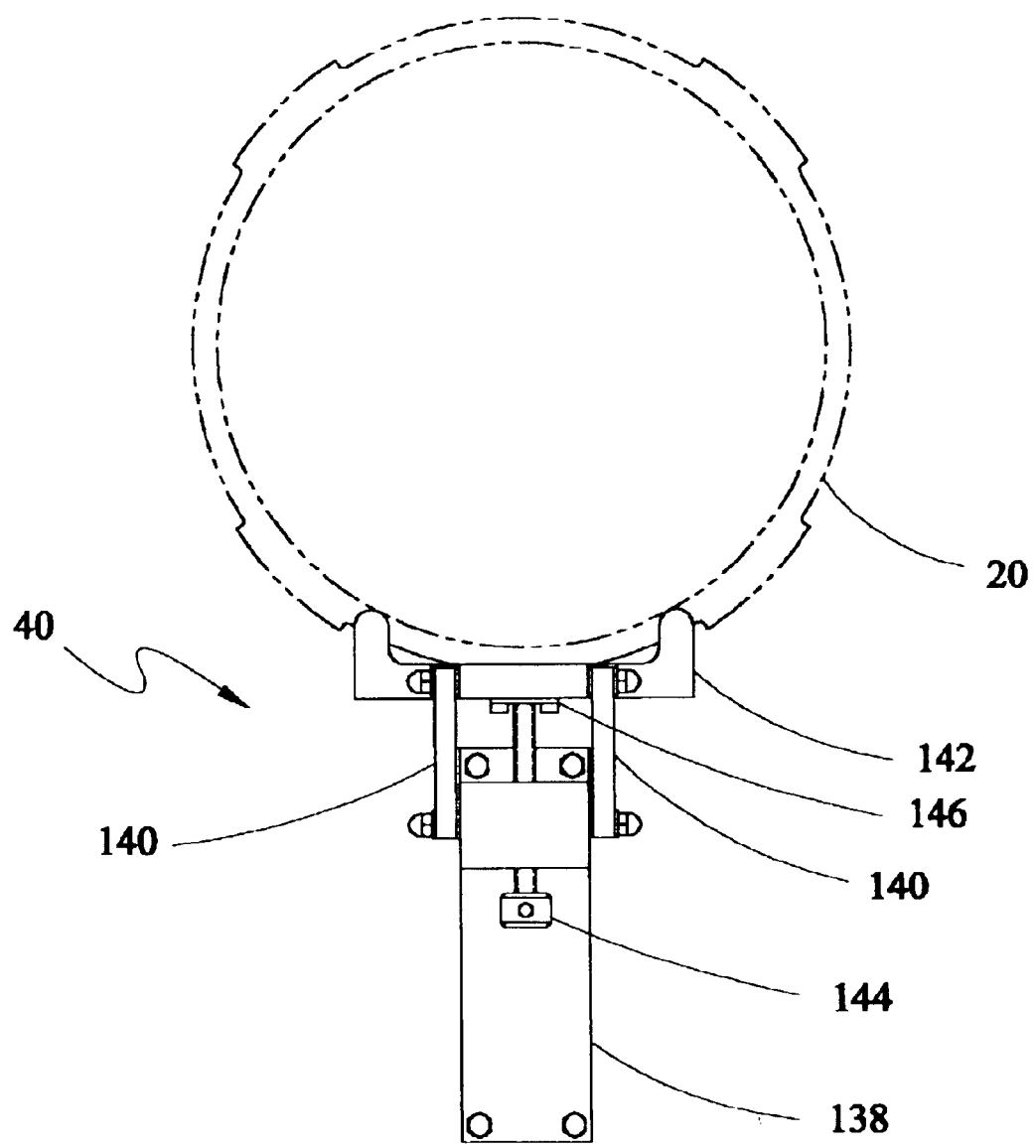
FIG. 9 is a front view of the present invention showing a close up of the container vertical support system. The container assembly is shown in phantom.

Referring now to FIGS. 8 and 9 the container support device 40 is shown in more detail. A support bracket 138 is attached to the front wall 46 of enclosure 12. A gasket 139 is positioned between support bracket 138 and front wall 46. Four linkages 140 are attached to support bracket 138 at one end and to a cradle 142 at the other end. Cradle 142 geometry tends to center the container 20 in the horizontal plane. Each linkage 140 is free to pivot at the point of connection to both the support bracket 138 and the cradle 142. The arrangement of the four linkages 140 permits raising and lowering of cradle 140 without introducing any angular displacement. A tee-screw 144 threads into support bracket 138 and contacts a wear pad 146. Wear pad 146 is fastened to the underside of cradle 142. Turning tee-screw 144 causes cradle 142 to raise and lower as desired.

Figure 10:
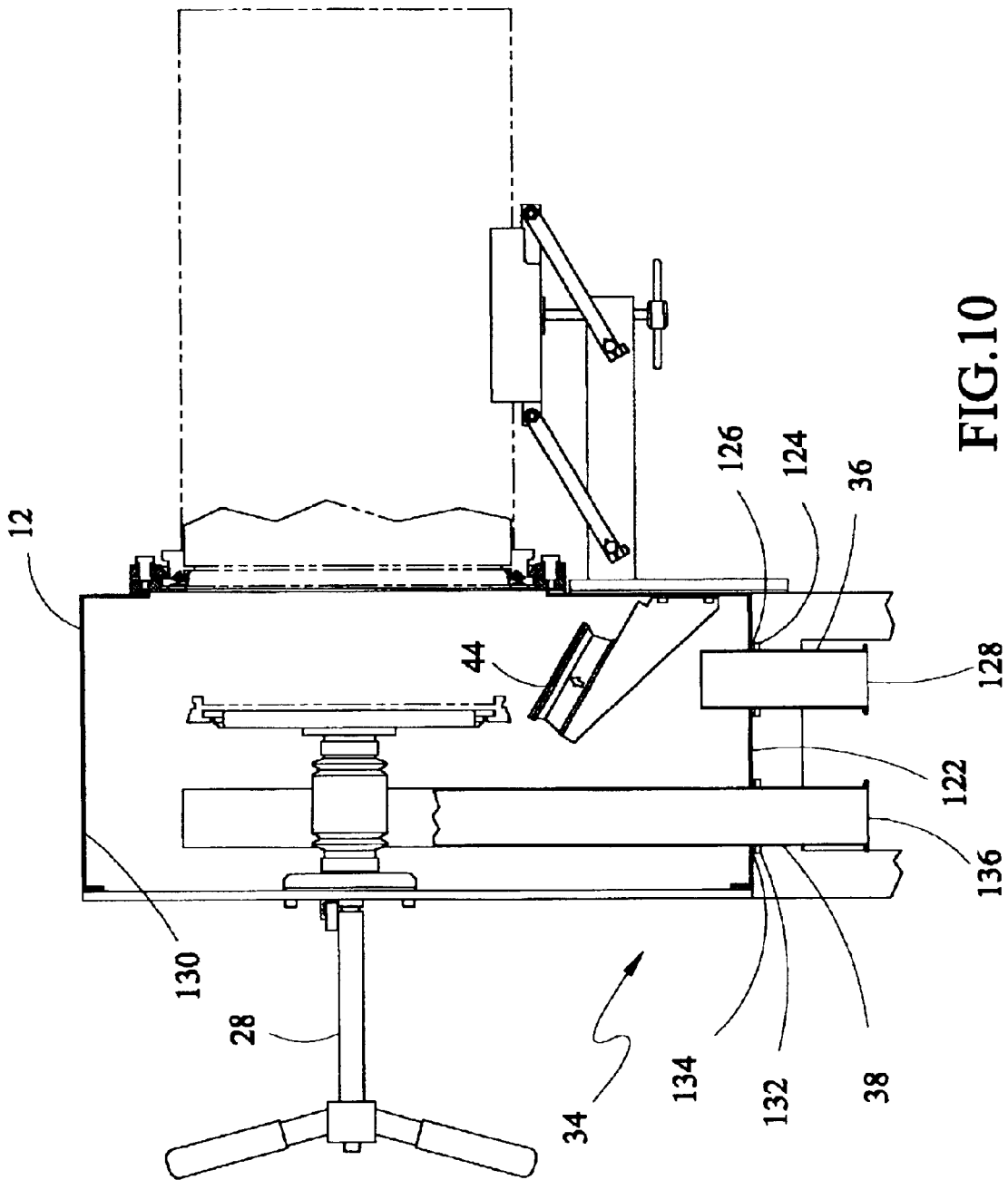
FIG. 10 is a close up side view of the present invention with its side cover removed and showing a close up of the VHP gas injection.

Referring now to FIG. 10 the vapor injection system 34 is shown in more detail. An inlet tube 36 protrudes through a bottom wall 122 of enclosure 12. The inlet tube 36 extends a relatively short distance, approximately 2 inches, within enclosure 12 causing the bactericide gas to be injected near mixing fan 44. Inlet tube 36 includes a flange 124 that is attached to the bottom wall 122 by suitable fasteners. A gasket 126 is positioned between flange 124 and bottom wall 122. Inlet tube 36 includes an interface flange 128 which may be such as those commonly referred to as "triclover flange". Interface flange 128 provides means for connecting to a bactericide vapor generation system further described below.

An outlet tube 38 protrudes through bottom wall 122 of enclosure 12. The outlet tube 38 extends a relatively long distance within enclosure 12 to close proximity, for example, approximately 4–5 inches, to an upper wall 130 of enclosure 12. (The total distance between the upper wall 130 and the bottom wall 122 may be, for example, 30 inches. Having the outlet tube 38 extend a relatively long distance into the enclosure 12 forces the bactericide vapor past the door removal system 28 and avoids a "short circuit" condition in which the bactericide vapor would exit the chamber immediately after being injected. Outlet tube 38 is similar to inlet tube 36 and includes a flange 132, gasket 134 and interface flange 136 which may be such as those commonly referred to as "triclover flange". Interface flange 136 also provides for connecting to a bactericide vapor generation system.

Figure 11:
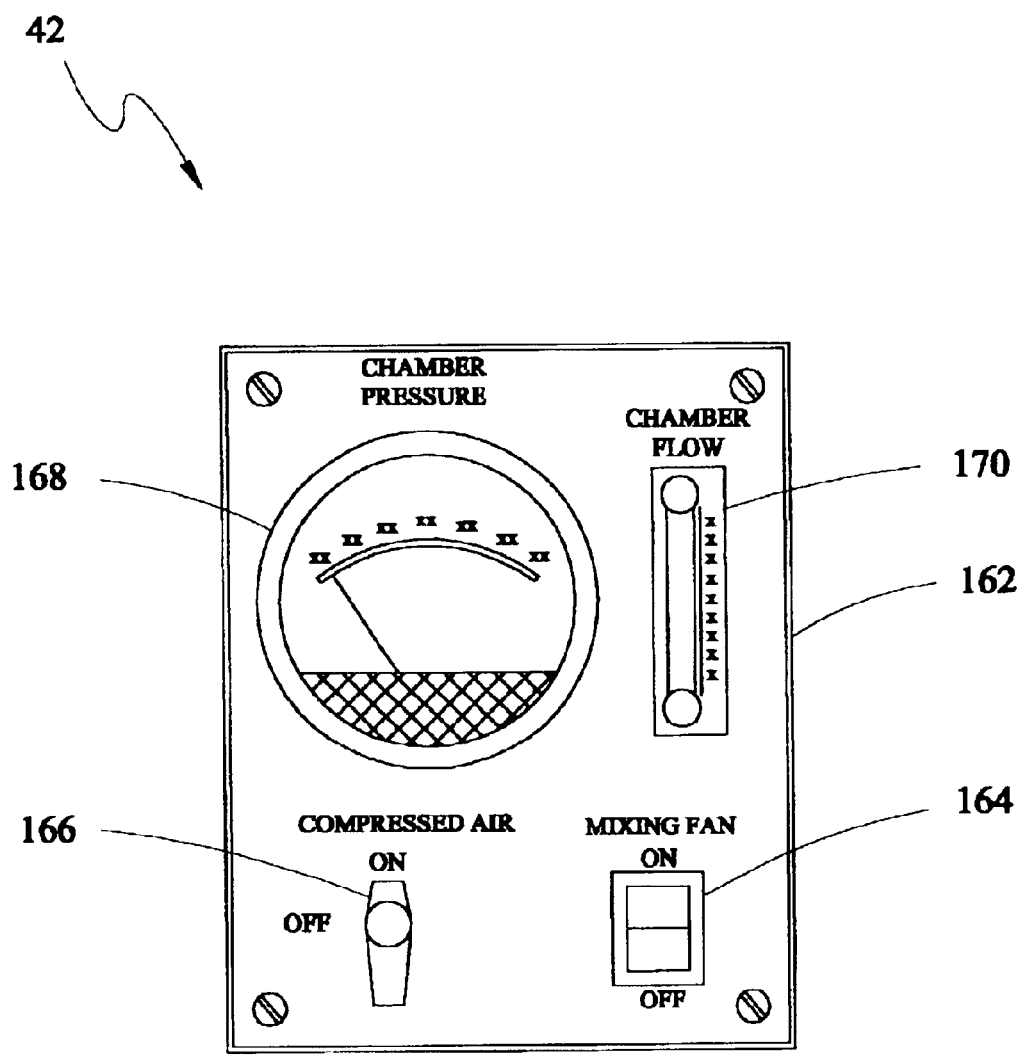
FIG. 11 is a close up front view of the electrical and pneumatic control enclosure of the present invention.
Figure 12:
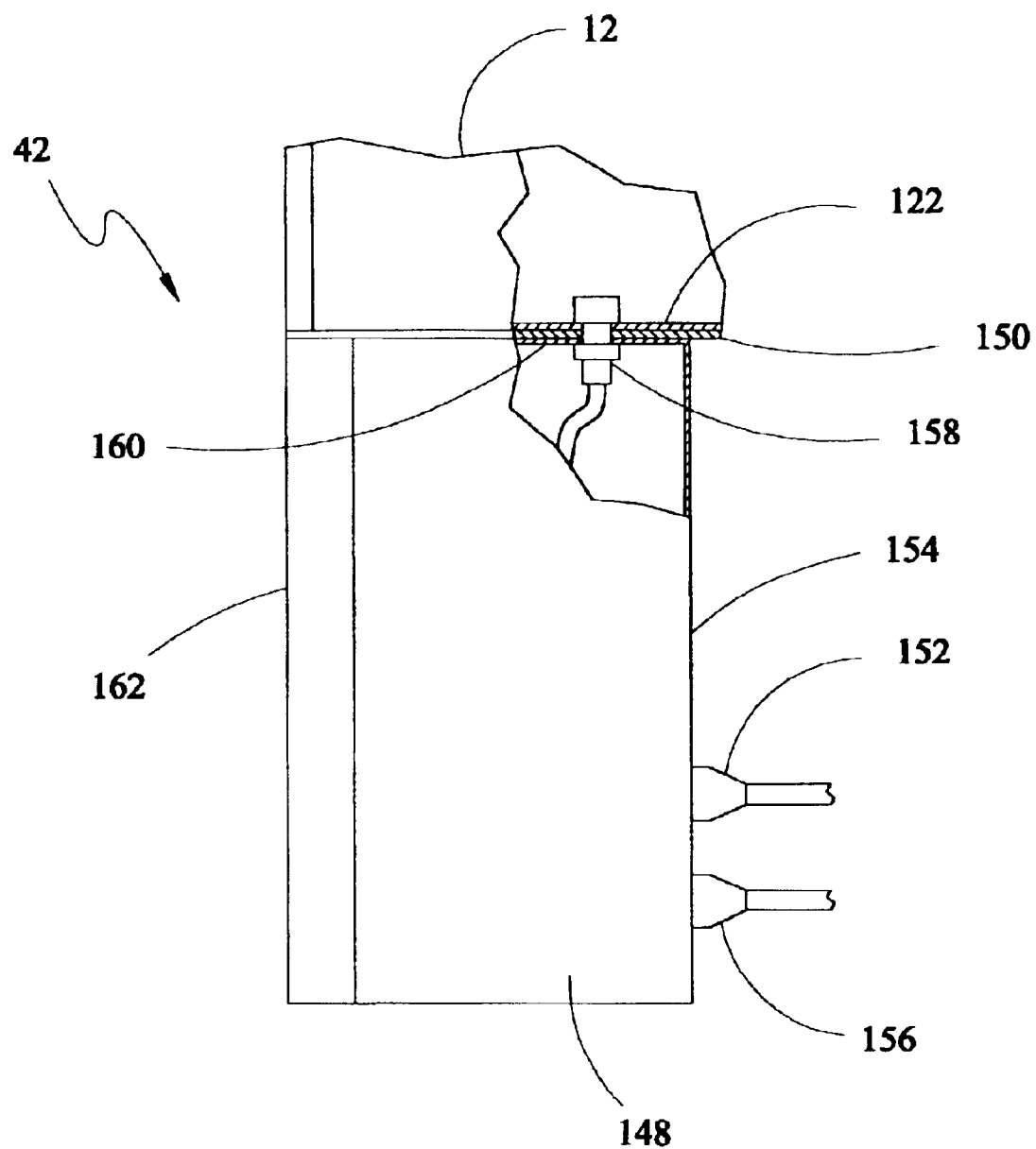
FIG. 12 is a close up side view of the electrical and pneumatic control enclosure of the present invention.

Referring now to FIGS. 11 and 12 the control box 42 is shown in more detail. A case 148 is attached to bottom wall 122 of enclosure 12. A gasket 150 is positioned between case 148 and bottom wall 122. A compressed air input connector 152 is mounted on a rear wall 154 of case 148. An electrical connector 156 is mounted on rear wall 154. A bulkhead connector 158 protrudes through an upper wall 160 of case 148, through gasket 150 and through bottom wall 122. Bulkhead connector 158 provides an air connection between closed volume 11 of enclosure 12 and the pneumatic components described below.

A front panel 162 of case 148 houses a power switch 164 which controls power to mixing fan 44, a compressed air on/off valve 166 which controls whether air is supplied to closed volume 11 of enclosure 12, a pressure gage 168 which displays the pressure within the enclosure 12, and a flow meter 170 which regulates the flow of air into the enclosure 12.

The container 20 provides the ability to transport and transfer sterile parts during manufacturing operations. Access to the internal volume of container 20 is possible via container door 30. The internal surfaces of container 20, the internal surface of container door 30 and the contact surfaces between the container 20 and the container door 30 must be decontaminated prior to container assembly use. This is necessary to avoid contamination of the sterile part to be contained therein. Removal of the container door 30 from the container 20 requires rotation of the container door relative to the container.

Decontamination of the internal surfaces of the container 20 requires exposing such surfaces to bactericide vapor. This is accomplished by use of the present invention.

Figure 13:
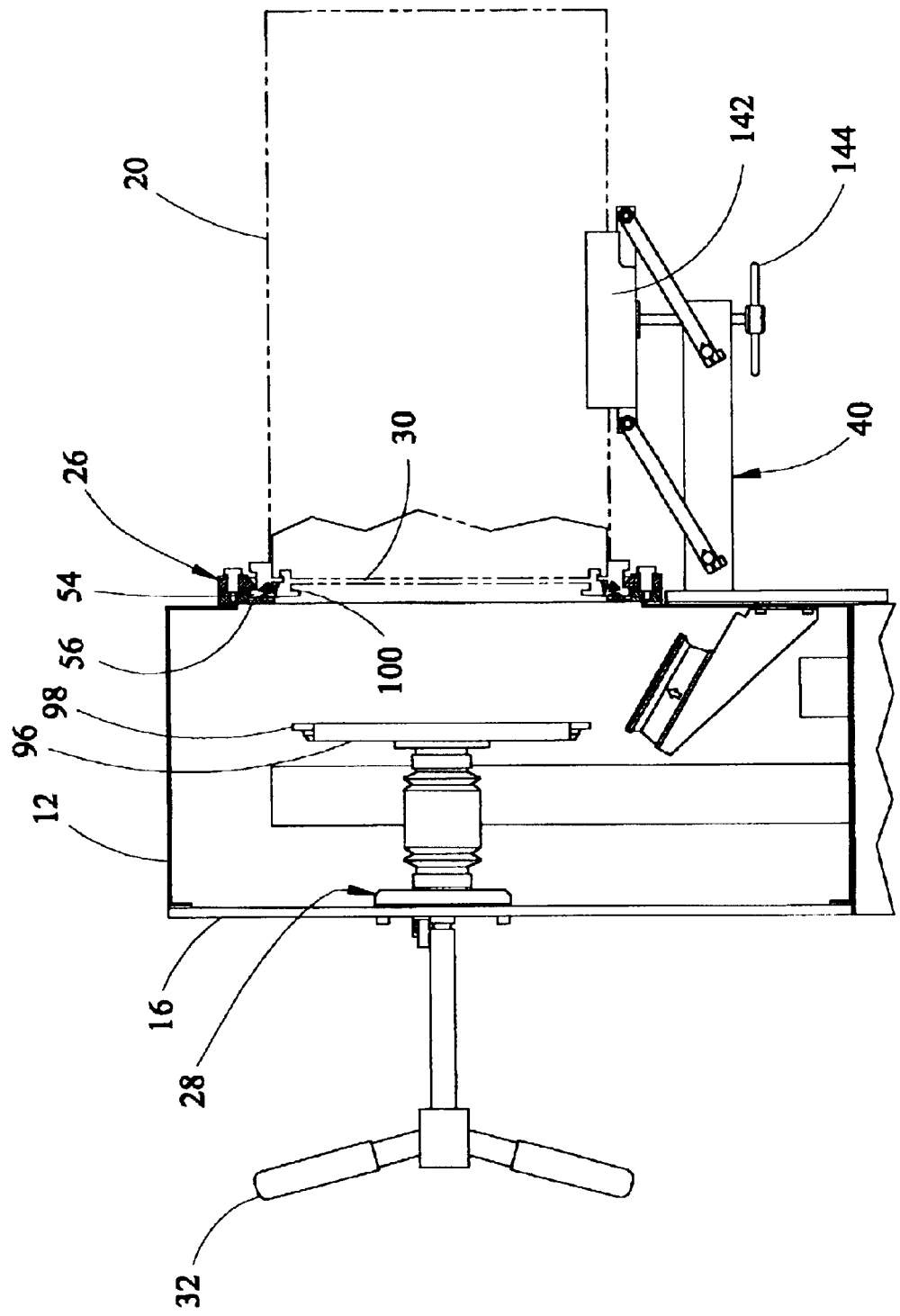
FIG. 13 is a close up side view of the present invention with its outer cover removed and shown in its "container just docked" configuration. The container assembly is shown in phantom.

During use, the operator places the container 20 onto cradle 142 of the container support device 40. The operator turns lifting handle 144 until he/she can visually align the forward flange 56 of container 20 with the receptacle 54 of container interface assembly 26. The operator manually slides the container assembly 20 into engagement with receptacle 54 and into contact with seal 58. The operator then actuates manual handle 70 to rotate rotatable ring 60 until lug 62 engages the forward flange 56 of the container 20. The operator then compresses seal 58 of the receptacle 54 by turning the lockdown nuts 74 of the lockdown fastener assemblies 72. At this point of the process, the system is in the "container just docked" configuration as shown in FIG. 13.

Figure 14:
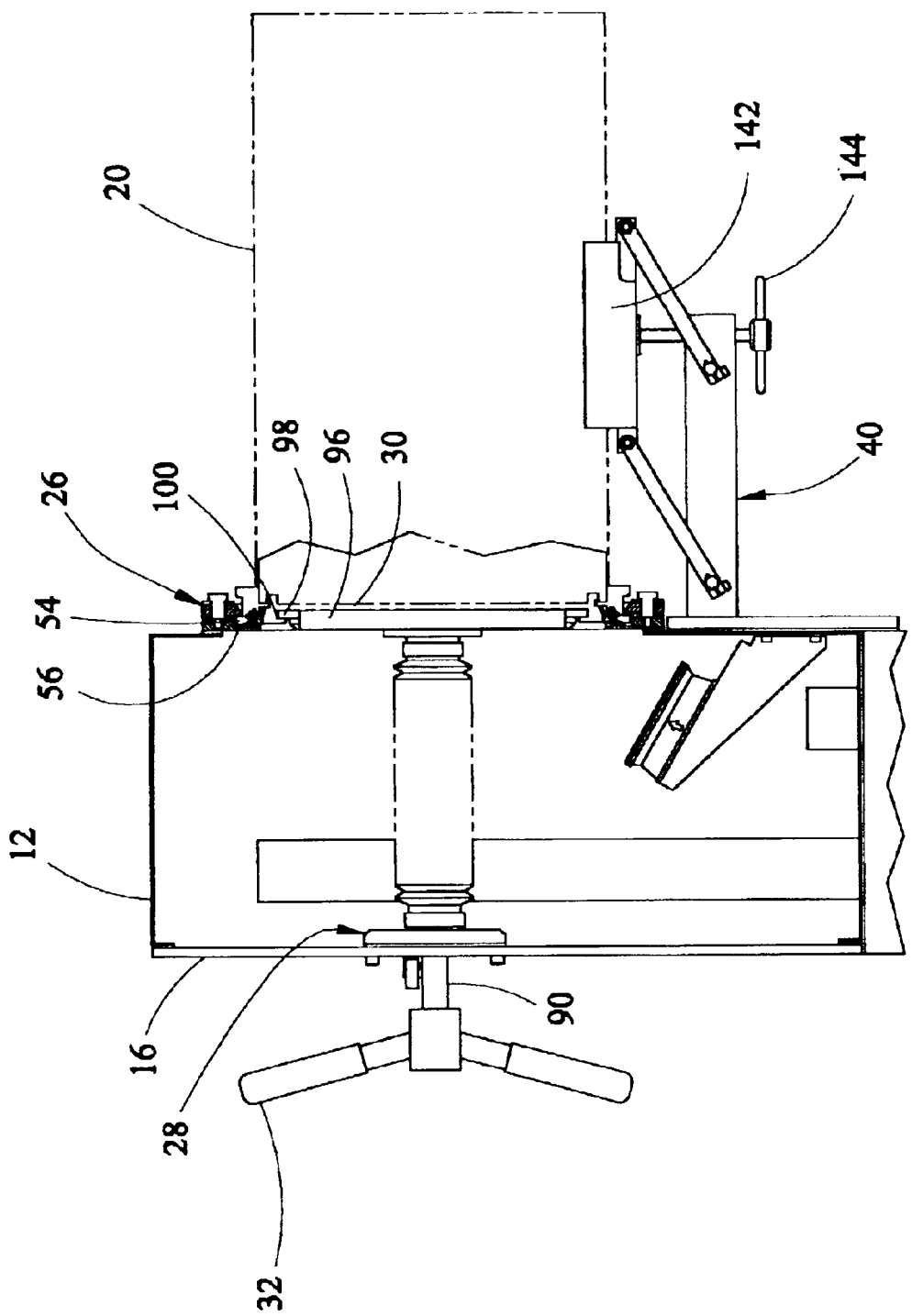
FIG. 14 is a closed up side view of the present invention with its outer cover removed and shown in its "container door ready to be removed" configuration. The container assembly is shown in phantom.

The operator uses the actuator element 32 external to enclosure 12 to manipulate the container door removal system 28 and remove the container door 30. The operator, using the transparent portion 16 of enclosure 12 to view the operation within, rotates and translates the actuator element 32 until the protrusions 98 of container door engagement plate 96 engage the door indentation 100. The system is now in the "container door ready to be removed" configuration, as shown in FIG. 14.

Figure 15:
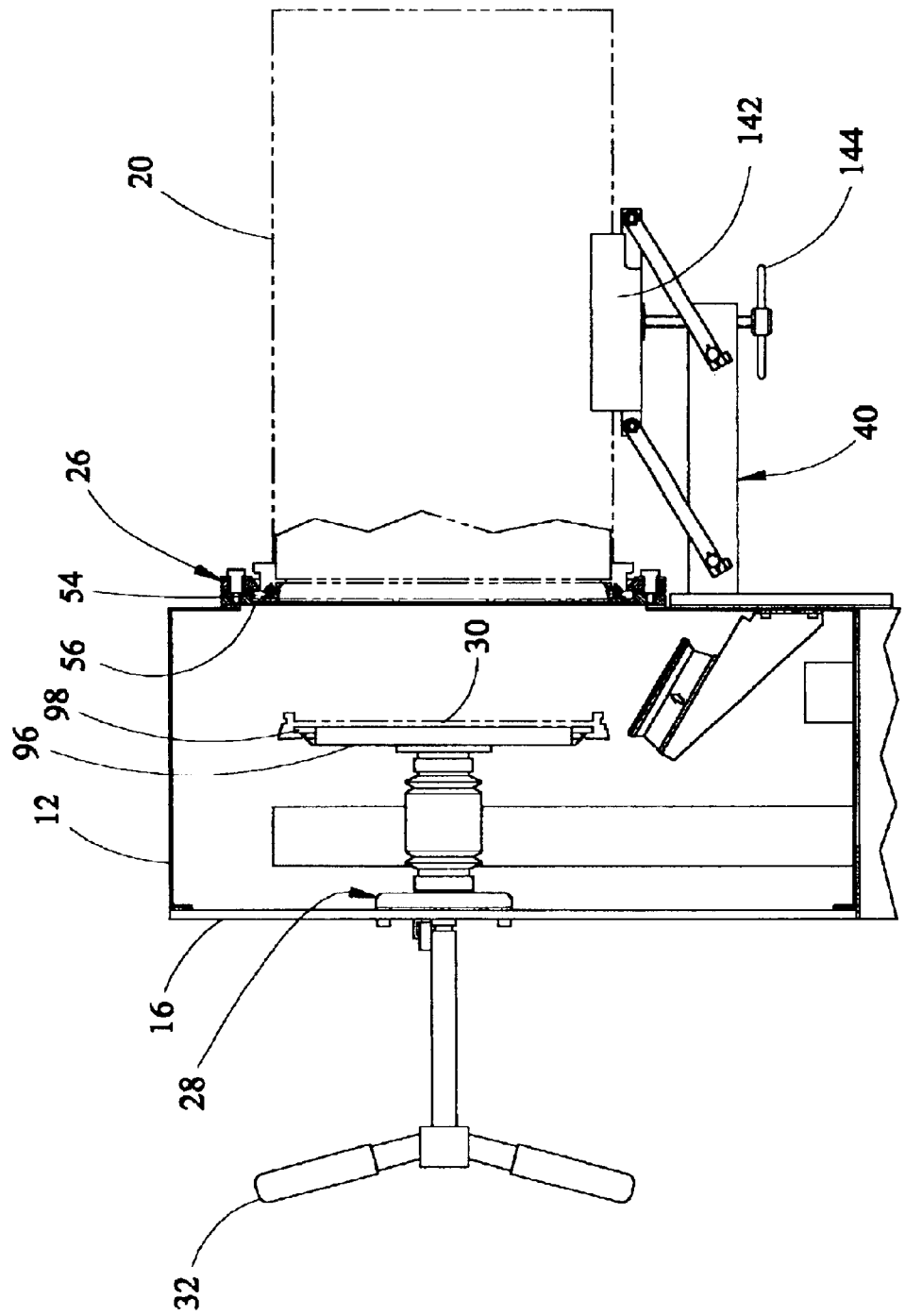
FIG. 15 is a close up side view of the present invention with its outer cover removed and shown in its "container door removed" configuration. The container assembly is shown in phantom.

The operator uses the actuator element 32 to turn the container door 30 until it disengages from the container 20, thus separating the two components. Shaft 90 of the container door removal system 28 is free to translate outward of the enclosure 12. The operator pulls the actuator element 32 until flat bar 114 of the shaft positioning system 112 engages the elongated indentation 120 of shaft 90. The system is now in the "container door removed" configuration as shown in FIG. 15.

The above description applies to those container assemblies that require rotation to remove the container door. Numerous types of container types and sizes exist today and the docking requirements might be of different nature than those described here.

The operator now runs a "leak test". This test permits to operator to determine whether it is safe to inject the enclosure 12, and container 20 attached, with bactericide vapor. The operator turns on the compressed air supply to the system by actuating the compressed air on/off valve 166 and adjusts the airflow into the enclosure using flow meter 170 until the required pressure value is displayed on pressure gage 168. If the airflow value necessary to set the internal pressure at the desired value is less that the maximum allowable value, the system may be considered leak free and bactericide vapor can be safely inject into it.

The operator then turns on the mixing fan 44 by actuating power switch 164.

The system is now ready for the decontamination cycle. The decontamination cycle is controlled solely by the vapor generator unit and may vary greatly depending on the vapor generator unit being used. In principal, the decontamination process of an enclosure consists of injecting bactericide vapor for a programmed length of time and then aerating the enclosure as required to purge all the vapor out.

Upon completion of the decontamination cycle, the operator reverses the steps described above. Container door 30 is installed back onto container 20 and the container is separated from the container interface assembly 26. Because the container door is installed on the container assembly, the surfaces and volume internal to the container are not exposed to contaminated external environments. The container assembly is now ready for use.

Figure 16:
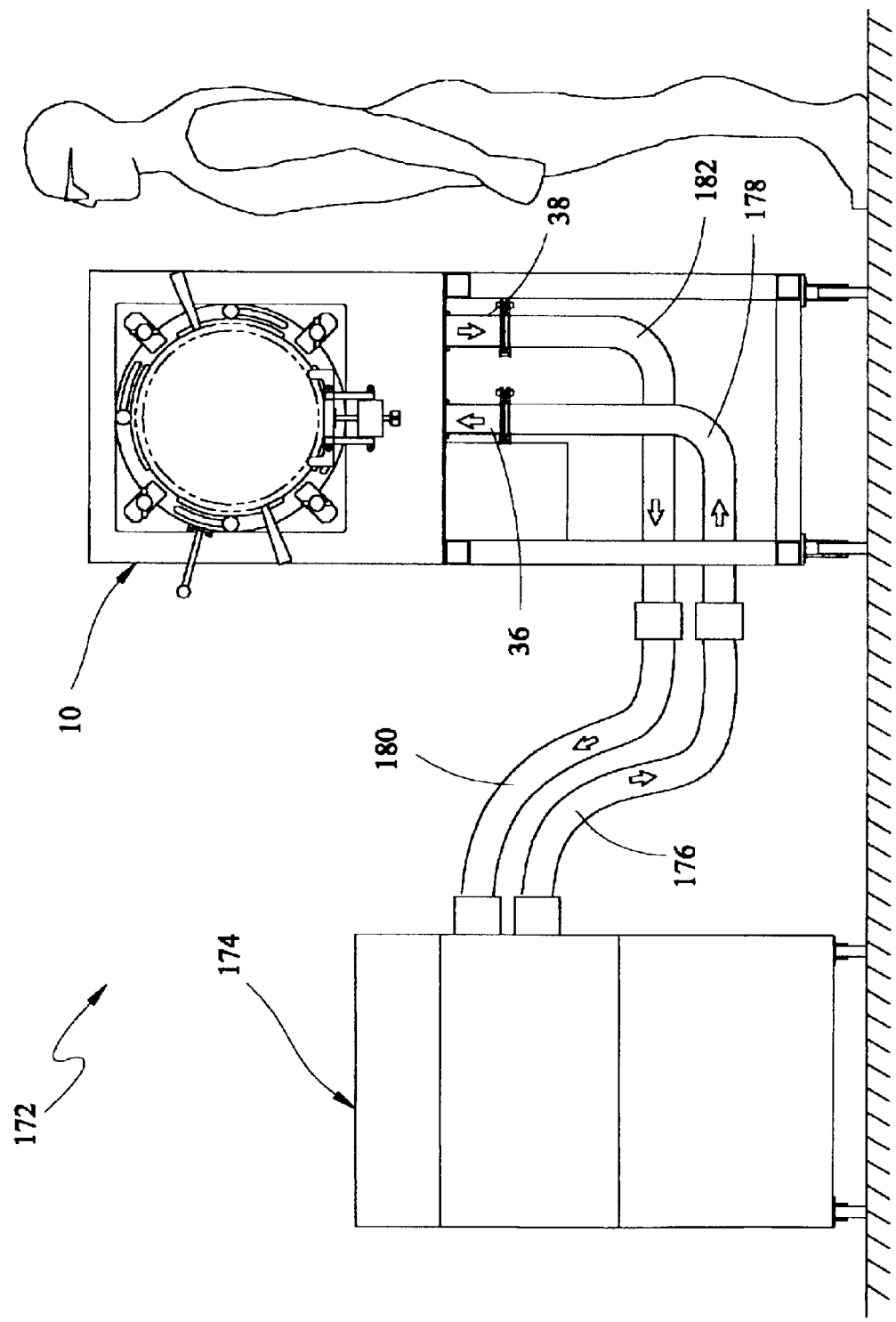
FIG. 16 is a system view in a single unit configuration.

Referring now to FIG. 16, an entire decontamination system for generating a bactericide vapor and decontaminating a container is illustrated, designated generally as 172. The decontamination system 172 includes a vapor generation system 174 for generating a bactericide vapor; and, a system for decontaminating a container, such as described above, and designated generally as 10. A flexible inlet hose 176 connects to a rigid inlet pipe section 178 which is attached to inlet 36 the vapor injection system 34. A flexible return hose 180 connects to a rigid return pipe section 182 which is attached to outlet 38. All connections are made by suitable connecting devices.

Bactericide vapor is generated inside the vapor generation system 174 and conveyed under slight pressure into the system 10 for decontaminating a container, via the flexible inlet hose 176 and rigid pipe section 178. The bactericide vapor is then conveyed back to the vapor generation system 174 via the rigid pipe section 182 and flexible return hose 180. The vapor generation system 174 circulates the bactericide vapor as described for the duration of the decontamination cycle.

Figure 17:
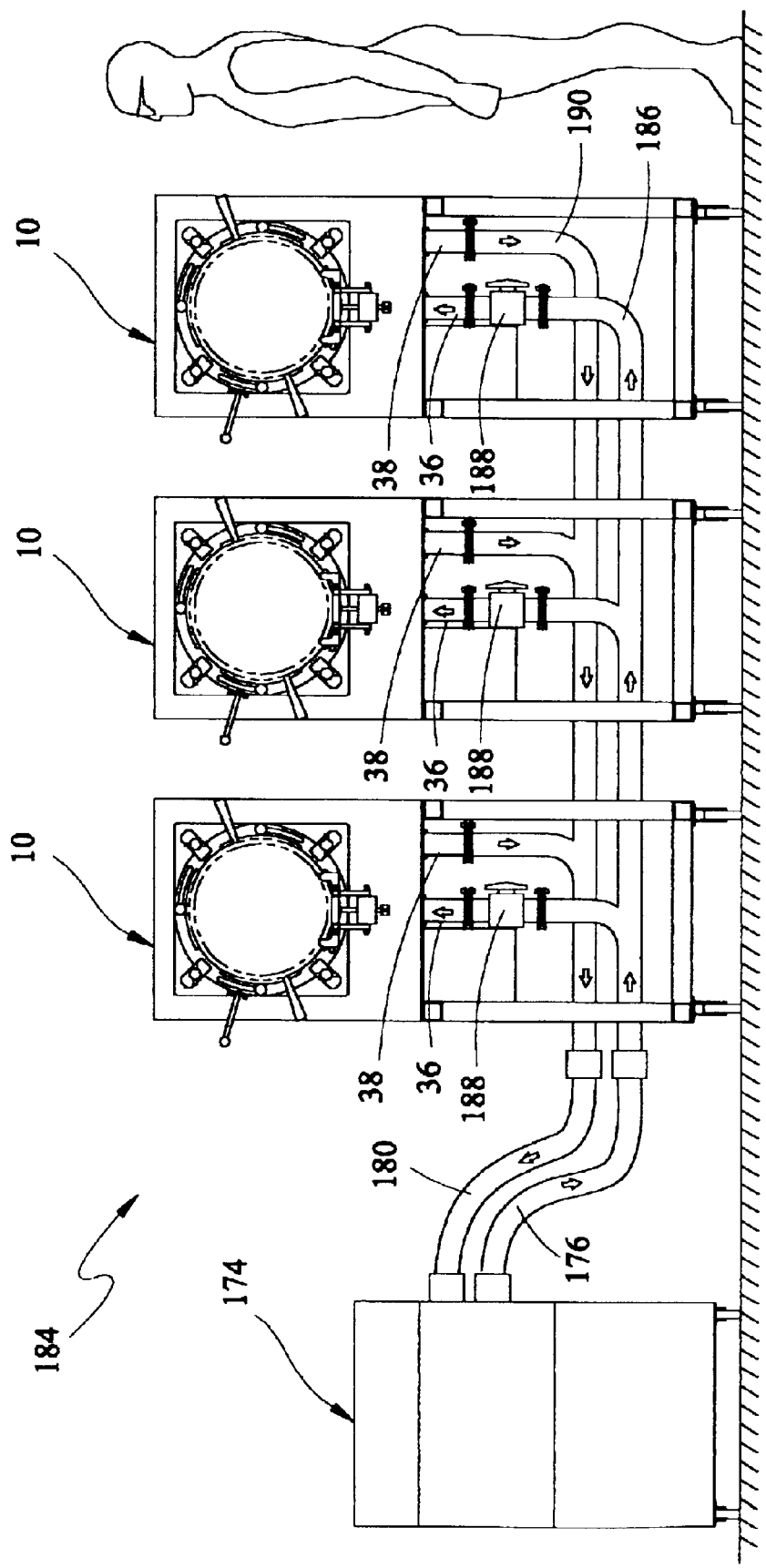
FIG. 17 is a system view in its multiple unit application.

Referring now to FIG. 17, a multi-unit decontamination system 184 is shown that includes a number of systems 10 for decontaminating associated containers and one vapor generation system 174. A flexible inlet hose 176 connects to a rigid inlet pipe manifold 186 which is attached to each inlet 36 via multiple manual flow control valves 188. A flexible return hose 180 connects to a rigid return pipe manifold 190 which is attached to each outlet 38. All connections are made by suitable connecting devices.

Bactericide vapor is generated inside the vapor generation system 174 and conveyed under slight pressure into each of the systems 10 for decontaminating a container via the flexible inlet hose 176 and rigid pipe manifold 178. The manual flow control valves 188 are provided to balance the flow of the bactericide vapor evenly amongst the systems 10. The bactericide vapor is then conveyed back to the vapor generation system 174 via the rigid pipe manifold 190 and flexible return hose 180. The vapor generation system 174 circulates the bactericide vapor as described for the duration of the decontamination cycle.

Although the invention here described is directed mostly for use in the pharmaceutical industry, it is understood that it is equally applicable to the medical devices industry, and any other industry requiring the decontamination of container with bactericide vapor.

Obviously, many modifications and variations of the present invention are possible in light of the above teachings. It is, therefore, to be understood that within the scope of the appended claims, the invention may be practiced otherwise than as specifically described.

What is claimed and desired to be secured by Letters Patent of the United States is:

1. A system for decontaminating a container of a type that interfaces with a rapid transfer port (RTP), comprising:
   a) an enclosure for providing a closed volume for bactericide vapor, said enclosure having a container access opening formed therein for providing vapor communication between a container and said closed volume;
   b) a container interface assembly at said container access opening for positioning, locking and sealing the container to said enclosure;
   c) a container door removal system partially contained within said enclosure, operably engaged with said enclosure and attachable to a container door of the container for separating the container door from the container, said container door removal system including an actuator element located external to said enclosure; and,
   d) a vapor injection system secured to said enclosure, comprising an inlet and an outlet for the bactericide vapor,
   wherein during operation a container is attached to said container interface assembly, the container door is separated from the container by operating said actuator element of said container door removal system, providing vapor communication between said closed volume and the volume within the container, and the bactericide vapor may be introduced into said enclosure and said container via said vapor injection system.

2. The system of claim 1, wherein said enclosure comprises:
   a stainless steel outer skin and a transparent portion therein, said transparent portion for providing an internal view of said enclosure.

3. The system of claim 1, further comprising:
   a welded tubular frame for supporting said enclosure.

4. The system of claim 1, further comprising:
   a container support device attached to said enclosure, said container support device being adjustable in a vertical direction for aligning the container to said container interface assembly.

5. The system of claim 1, further comprising:
   a control box operatively associated with said enclosure; and,
   control components housed within said control box, said control components comprising a mixing fan electrical control and pneumatic components for providing a system leak test.

6. The system of claim 1, further comprising:
   a mixing fan contained within said enclosure, said mixing fan being angled to maximize mixing of bactericide vapor within said enclosure.

7. The system of claim 1, wherein said container interface assembly comprises:
   a) an interface plate attached to a front wall of said enclosure, said interface plate forming a receptacle for a forward flange of the container;
   b) a seal for creating an airtight connection between said receptacle and said forward flange;
   c) a rotatable ring for engaging said forward flange; and,
   d) a set of lockdown fastener assemblies which are connected to said interface plate for compressing said rotatable ring onto said forward flange.

8. The system of claim 1, wherein said container door removal system comprises:
   a) a flanged cylindrical member in fixed engagement with a rear wall of said enclosure;
   b) a shaft positioned within and in sliding engagement with said flanged cylindrical member, said shaft having a shaft external end and a shaft internal end, said actuator element being attached to said shaft external end;
   c) a container door engagement plate in fixed engagement with said shaft internal end; and,
   d) a bellows being attached at a first end to said flanged cylindrical member and at a second end to said shaft internal end.

9. The system of claim 8, wherein said container door removal system further comprises:
   a shaft positioning system comprising a flat bar attached to said enclosure rear wall, wherein said flat bar is movable in the vertical direction for engagement with an elongated indentation along the length of said shaft, thus providing desired positioning of said shaft.

10. The system of claim 1, wherein said vapor injection system comprises:
    a) an inlet tube protruding through a bottom wall of said enclosure and extending a relatively short distance from said bottom wall, said inlet tube being said inlet; and,
    b) an outlet tube protruding through said bottom wall and extending a relatively long distance within said enclosure to close proximity to an upper wall of said enclosure, said outlet tube being said outlet.

11. A decontamination system for generating a bactericide vapor and decontaminating a container, said container of a type that interfaces with a rapid transfer port, said decontamination system, comprising:
    a vapor generation system for generating bactericide vapor; and,
    at least one system for decontaminating a container of a type that interfaces with a rapid transfer port (RTP), comprising:
    a) an enclosure for providing a closed volume for bactericide vapor, said enclosure having a container access opening formed therein for providing vapor communication between a container and said closed volume
    b) a container interface assembly at said container access opening for positioning, locking and sealing the container to said enclosure;
    c) a container door removal system partially contained within said enclosure, operably engaged with said enclosure and attachable to a container door of the container for separating the container door from the container, said container door removal system including an actuator element located external to said enclosure; and, d) a vapor injection system secured to said enclosure, comprising an inlet and an outlet in fluid communication with said vapor generating system for providing said bactericide vapor, wherein during operation a container is attached to said container interface assembly, the container door is separated from the container by operating said actuator element of said container door removal system, providing vapor communication between said closed volume and the volume within the container, and the bactericide vapor may be introduced into said enclosure and said container via said vapor injection system.

12. The decontamination system of claim 11, wherein said at least one system for decontaminating a container comprises a plurality of systems for decontaminating associated containers.

13. The decontamination system of claim 11, wherein said enclosure comprises:

a stainless steel outer skin and a transparent portion therein, said transparent portion for providing an internal view of said enclosure.

14. The decontamination system of claim 11, further comprising:

a welded tubular frame for supporting said enclosure.

15. The decontamination system of claim 11, further comprising:

a container support device attached to said enclosure, said container support device being adjustable in a vertical direction for aligning the container to said container interface assembly.

16. The decontamination system of claim 11, further comprising:

a control box operatively associated with said enclosure; and, control components housed within said control box, said control components comprising a mixing fan electrical control and pneumatic components for providing a system leak test.

17. The decontamination system of claim 11, further comprising:

a mixing fan contained within said enclosure, said mixing fan being angled to maximize mixing of bactericide vapor within said enclosure.

18. The decontamination system of claim 11, wherein said container interface assembly comprises:

a) an interface plate attached to a front wall of said enclosure, said interface plate forming a receptacle for a forward flange of the container;

b) a seal for creating an airtight connection between said receptacle and said forward flange;

c) a rotatable ring for engaging said forward flange; and, d) a set of lockdown fastener assemblies which are connected to said interface plate for compressing said rotatable ring onto said forward flange.

19. The decontamination system of claim 11, wherein said container door removal system comprises:

a) a flanged cylindrical member in fixed engagement with a rear wall of said enclosure;

b) a shaft positioned within and in sliding engagement with said flanged cylindrical member, said shaft having a shaft external end and a shaft internal end, said actuator element being attached to said shaft external end;

c) a container door engagement plate in fixed engagement with said shaft internal end; and, d) a bellows being attached at a first end to said flanged cylindrical member and at a second end to said shaft internal end.

20. The decontamination system of claim 19, wherein said container door removal system further comprises:

a shaft positioning system comprising a flat bar attached to said enclosure rear wall, wherein said flat bar is movable in the vertical direction for engagement with an elongated indentation along the length of said shaft, thus providing desired positioning of said shaft.

21. The decontamination system of claim 11, wherein said vapor injection system comprises:

a) an inlet tube protruding through a bottom wall of said enclosure and extending a relatively short distance from said bottom wall, said inlet tube being said inlet; and, b) an outlet tube protruding through said bottom wall and extending a relatively long distance within said enclosure to close proximity to an upper wall of said enclosure, said outlet tube being said outlet.

* * * * *

UNITED STATES PATENT AND TRADEMARK OFFICE
CERTIFICATE OF CORRECTION

PATENT NO. : 6,969,497 B2
DATED : November 29, 2005
INVENTOR(S) : Giuseppe Sacca It is certified that error appears in the above-identified patent and that said Letters Patent is hereby corrected as shown below:

Column 9,
Line 37, after "system" insert -- , --.
Line 38, delete "for" and substitute -- in fluid communication with said enclosure for transferring --.

Signed and Sealed this

Twenty-first Day of February, 2006

JON W. DUDAS
*Director of the United States Patent and Trademark Office*